(12) United States Patent
Kell et al.

(10) Patent No.: US 8,215,159 B2
(45) Date of Patent: Jul. 10, 2012

(54) INSPECTION OF HOLES

(75) Inventors: James Kell, Nottingham (GB); Daniel Clark, Belper (GB)

(73) Assignee: Rolls-Royce PLC, London (GB)

( * ) Notice: Subject to any disclaimer, the term of this patent is extended or adjusted under 35 U.S.C. 154(b) by 98 days.

(21) Appl. No.: 12/850,955

(22) Filed: Aug. 5, 2010

(65) Prior Publication Data

US 2011/0048117 A1 Mar. 3, 2011

(30) Foreign Application Priority Data

Aug. 27, 2009 (GB) .................................. 0914904.8

(51) Int. Cl.
*G01M 15/14* (2006.01)
(52) U.S. Cl. .................................................. 73/112.01
(58) Field of Classification Search ............... 73/112.01, 73/112.03, 112.05, 112.06
See application file for complete search history.

(56) References Cited

U.S. PATENT DOCUMENTS

| | | | |
|---|---|---|---|
| 3,566,669 A * | 3/1971 | Lawrence et al. .................. 374/5 |
| 3,990,301 A | 11/1976 | Smith | |
| 4,139,822 A | 2/1979 | Urich et al. | |
| 4,198,852 A | 4/1980 | Osman et al. | |
| 4,644,162 A | 2/1987 | Bantel et al. | |
| 5,054,087 A * | 10/1991 | Carbon et al. ................ 382/152 |
| 5,111,046 A | 5/1992 | Bantel | |
| 5,773,790 A * | 6/1998 | Moore et al. ............. 219/121.71 |
| 6,153,889 A * | 11/2000 | Jones ........................ 250/559.45 |
| 6,524,395 B1 | 2/2003 | Devine, II | |
| 7,095,495 B2 * | 8/2006 | Bowles et al. ............. 356/237.6 |
| 7,579,830 B2 * | 8/2009 | Roney et al. ................... 324/238 |
| 7,651,261 B2 * | 1/2010 | Bunker et al. ................... 374/43 |
| 7,890,274 B2 * | 2/2011 | Bunker et al. .................. 702/45 |
| 7,909,507 B2 * | 3/2011 | Bunker et al. ................ 374/121 |
| 2004/0149905 A1 | 8/2004 | Bowles et al. | |

FOREIGN PATENT DOCUMENTS

| | | |
|---|---|---|
| EP | 0 943 916 A2 | 9/1999 |
| FR | 2 871 568 | 12/2005 |
| GB | 2 125 556 A | 3/1984 |
| JP | A-2001-201494 | 7/2001 |
| JP | A-2005-123101 | 5/2005 |

OTHER PUBLICATIONS

British Search Report for British Patent Application No. 0914904.8, dated Oct. 27, 2009.
Jan. 18, 2011 British Search Report issued in British Patent Application No. GB1013140.7.

* cited by examiner

*Primary Examiner* — Freddie Kirland, III
(74) *Attorney, Agent, or Firm* — Oliff & Berridge, PLC

(57) ABSTRACT

A method of inspecting a hole defined by a component situated within an engine, the engine including a chamber configured to receive fluid from a fluid supply, wherein the component is in flow communication with the fluid supply via the chamber, the method includes the steps of: (i) delivering a test fluid via the chamber to the component to induce flow of the test fluid through the hole; (ii) deploying a sensor panel adjacent to the component in a path of test fluid issuing from the hole, the sensor panel being sensitive to impingement of the test fluid; and (iii) assessing a condition of the hole depending on a response of the sensor panel at a location corresponding to the hole.

15 Claims, 2 Drawing Sheets

INSPECTION OF HOLES

BACKGROUND

This invention relates to a method of inspecting a hole in a component, and to a device for use in such a method. The invention is particularly, although not exclusively, concerned with the in situ inspection of holes in components of gas turbine engines.

Many components of gas turbine engines, such as turbine vanes and blades, and combustor components, are exposed to very high temperatures in operation of the engine, which can be close to or exceed the melting point of the material from which the component is made. It is well known to cool such components by means of high pressure air taken from the compressor of the engine and ducted to the component. For this purpose, turbine blades and vanes may have internal cavities to which the cooling air is supplied, and holes which extend from the cavity to the outside surface of the blade through which the cooling air can pass to rejoin the main gas flow through the engine. The cooling air not only extracts heat from the blade or vane as it passes through the cavity and the cooling holes, but also forms a film of cooler air over the surface of the blade, shielding it from the hot gas flow.

Holes are disposed in an array on the surface of the vane or blade, and the disposition of the holes in the array is carefully determined in order to provide the maximum cooling effect with minimum use of cooling air. If a hole becomes blocked, for example by debris entering the cooling air supply, the temperature of the surrounding surface of the blade or vane will increase. If enough holes become blocked, the resulting temperature increase can lead to failure of the material of the blade or vane, which can result in failure of the component itself, and possibly the entire engine. It is therefore desirable to inspect cooling holes in such components, and particularly aerofoil components such as turbine blades and vanes, to check that the cooling holes remain sufficiently clear so that they can perform their intended cooling function.

Various cooling hole inspection techniques have been proposed, for example in U.S. Pat. No. 4,644,162, U.S. Pat. No. 5,111,046 and U.S. Pat. No. 6,524,395. The known techniques all require the inspected component to be removed from the engine. Strip down of a gas turbine engine to the extent required to remove turbine blades and vanes is very time consuming and expensive, and consequently extensive cooling hole inspection is not currently practical between major engine overhauls.

SUMMARY

According to the present invention there is provided a method of inspecting a hole in a component situated within an engine, the engine comprising a chamber configured to receive fluid from a fluid supply, wherein the component is in flow communication with the fluid supply via the chamber, the method comprising:
(i) delivering a test fluid via the chamber to the component to induce flow of the test fluid through the hole;
(ii) deploying a sensor panel adjacent the component in the path of test fluid issuing from the hole, the sensor panel being sensitive to the impingement of the test fluid; and
(iii) assessing the condition of the hole in dependence on the response of the sensor panel at the location corresponding to the hole.

A method in accordance with the present invention is particularly suitable when the hole is one of an array of holes, in which case the sensor panel may be of a sufficient size to extend into the paths of test fluid issuing from a plurality, and possibly all, of the holes of the array.

Various test fluids may be employed, in conjunction with a sensor panel, which is sensitive to the impingement of the respective test fluid. In one embodiment, the test fluid is steam.

The sensor panel may comprise a sheet impregnated with an indicator composition which changes state upon impingement by the test fluid. The indicator composition may be a universal indicator solution which undergoes a colour change when subjected to impingement by the test fluid, such as steam.

The sensor panel may comprise a sheet of absorbent material such as a woven or non-woven textile material, or paper. The sensor panel may also include a backing material, such as a fine gauze or mesh to support the sheet in a desired configuration to match the profile of a surface of the component in which the hole, or the array of holes, is provided.

In an alternative method, the sensor panel may comprise an array of electromechanical transducers, each of which can generate an electrical signal on impingement of the test fluid. The disposition of the transducers in the transducer array may correspond to the disposition of holes in the hole array.

The sensor panel may be supported by a frame. The frame may be of variable geometry so that it can assume a collapsed condition and a deployed condition. Thus, the frame, with the sensor panel, can be delivered to a position adjacent a component inside a gas turbine engine or other machine in the collapsed condition, and then transformed into the deployed condition when in the desired position. The frame may have locating means for cooperation with the component to locate the deployed sensor panel in a desired position with respect to the component.

While a method in accordance with the present invention may be employed to inspect one or more holes in a component when in situ within a machine, or after removal from the machine, a method in accordance with the present invention is particularly suitable for the in situ inspection of a hole, or array of holes, in a component while in situ in a gas turbine engine. More specifically, a method in accordance with the present invention is suitable for inspecting cooling holes in an aerofoil component of the gas turbine engine. The method is also suitable for inspecting holes in components which are present for purposes other than cooling, for example for supplying air for air bearings.

The present invention also provides a device for conducting a method as defined above, the device comprising a sensor panel which is sensitive to the impingement of the test fluid. The device may comprise a frame of variable geometry which carries the sensor panel.

BRIEF DESCRIPTION OF THE DRAWINGS

For a better understanding of the present invention, and to show more clearly how it may be carried into effect, reference will now be made, by way of example, to the accompanying drawings, in which.

DETAILED DESCRIPTION OF EMBODIMENTS

Figure 1:
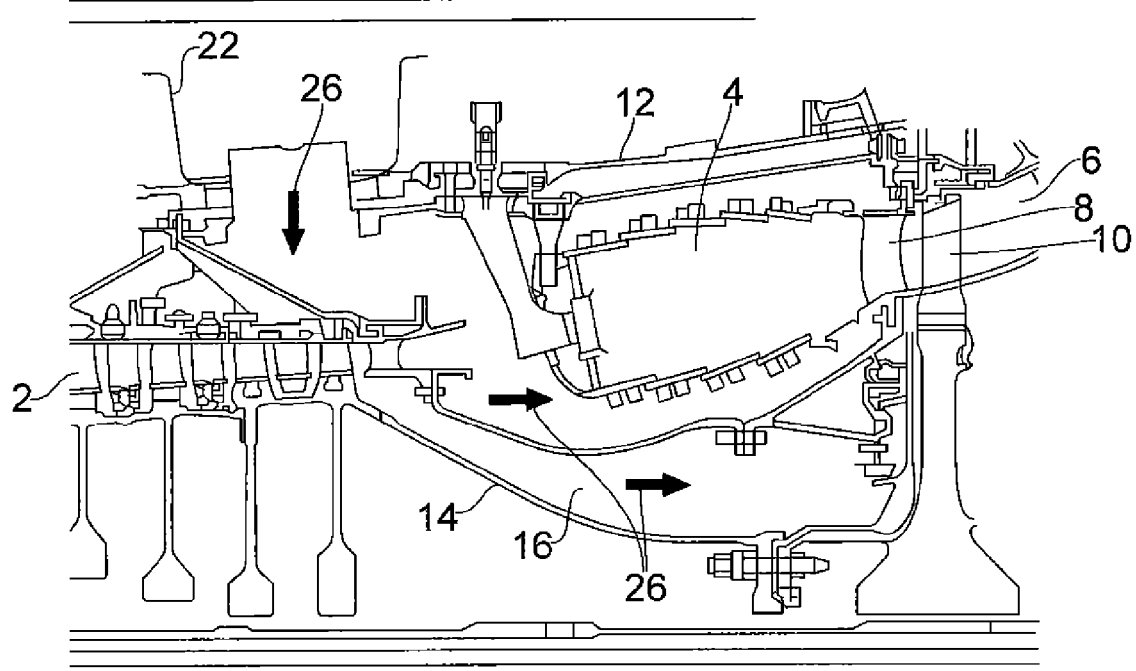
FIG. 1 is a partial sectional view of a gas turbine engine.

FIG. 1 shows part of a compressor 2, a combustor 4 and a high pressure (HP) turbine stage 6 of a gas turbine engine. The HP turbine stage comprises a nozzle guide vane 8 and a turbine blade 10. In operation of the engine, as is well known, air is compressed by the compressor 2 and supplied to the combustor 4, where it is mixed with fuel and ignited. The combustion products then flow through the HP turbine 6, and other turbine stages, to generate power.

Figure 2:
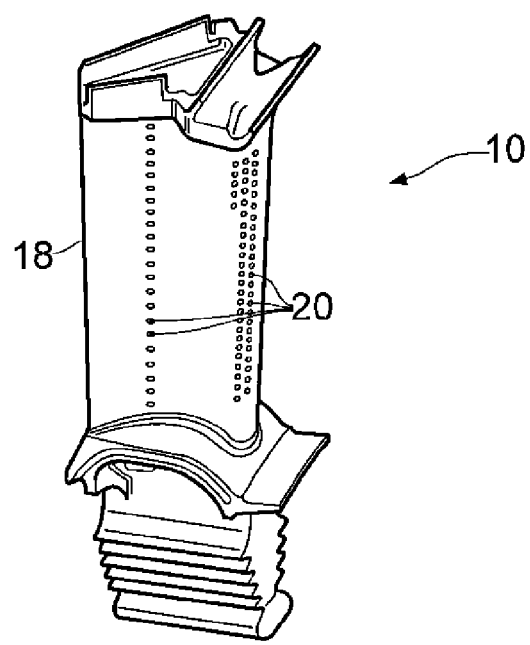
FIG. 2 shows a turbine blade of the engine of FIG. 1.

The compressor 2, the turbine 6 and the combustor 4 are situated within an engine casing 12. A partition 14 defines a chamber (or "duct") 16 which receives high pressure air from the compressor 2. The majority of this air is directed to the combustor 4, but some serves as cooling air and is conveyed via the chamber (or "duct") 16, for example, to the vane 8 and the blade 10 for this purpose. The blade 10 is shown in FIG. 2, and comprises an aerofoil section 18 having one or more internal cavities (not shown) which receive air from the chamber 16. The air circulates within the aerofoil section 18 and is eventually discharged into the main gas flow through the engine via an array of cooling holes 20.

In the same manner, the vane 8 also has one or more internal cavities and cooling holes corresponding to the cooling holes 20.

In operation, cooling air issuing from the holes 20 forms a film of relatively cool air over the surface of the aerofoil section 18, shielding it from the hot gases issuing from the combustor 4. Complete or partial blockage of any of the holes 20 reduces the volume of issuing air forming the film, and so can result in overheating of the material of the blade 10 (or vane 8). Misshapen holes, for example due to erosion, damage or manufacturing error, may also effect the flow rate of air passing through the holes, and hence result in under or over cooling of the material of the blade 10 (or vane 8). However, it will be appreciated that it is difficult, or impossible, to inspect the condition of the holes 20 using conventional means while the vane 8 and blade 10 are situated within the engine.

A bleed valve arrangement 22, represented only partially in FIG. 1, includes a bleed valve (not shown) which enables air from the chamber 16 to be discharged, in some operating conditions of the engine, to a bypass duct (not shown).

In accordance with the present invention, the condition of the holes 20 is assessed as follows.

Figure 3:
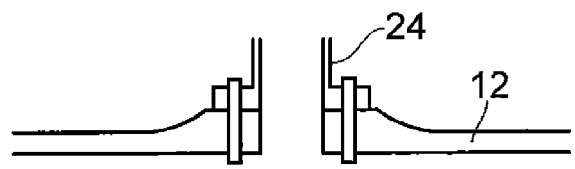
FIG. 3 is a schematic view of a bypass opening of the gas turbine engine of FIG. 1.

With the bleed valve of the bleed valve arrangement 22 removed, a steam line 24 (FIG. 3) is fitted to the engine casing 12 and steam at an elevated pressure is introduced into the chamber 16 as indicated by arrows 26. This steam thus enters the cavities in the vane 8 and the blade 10, and issues from the holes 20.

Figure 6:
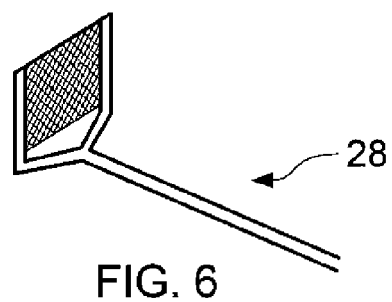
FIGS. 6 and 7 show the device of FIG. 5 in different configurations.
Figure 7:
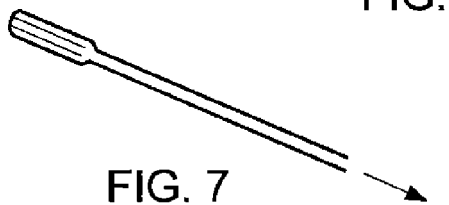

An inspection device 28 (FIGS. 4 to 7) is introduced into the engine by any suitable route and deployed to detect the steam issuing from the holes 20 of the vane 8 or blade 10. It will be appreciated from FIGS. 6 and 7 that the device 28 can be transformed from a collapsed condition shown in FIG. 7 to a deployed configuration shown in FIG. 6. In the collapsed condition shown in FIG. 7, the device has a small profile and so can be inserted into the engine through a relatively small opening, or along a relatively convoluted passage. Routing and final positioning of the device 28 can be assisted visually by means of, for example, a borescope.

Figure 4:
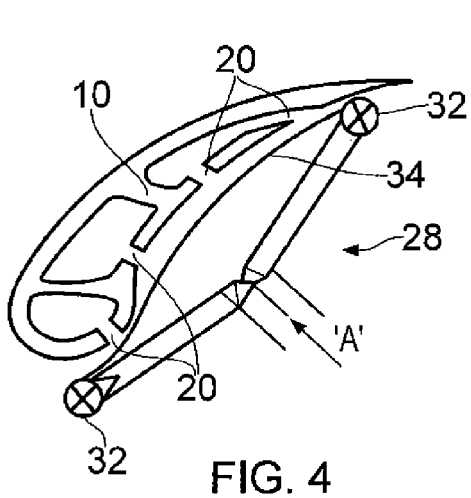
FIG. 4 represents the blade of FIG. 2 in conjunction with a device for inspecting cooling holes of the blade.
Figure 5:
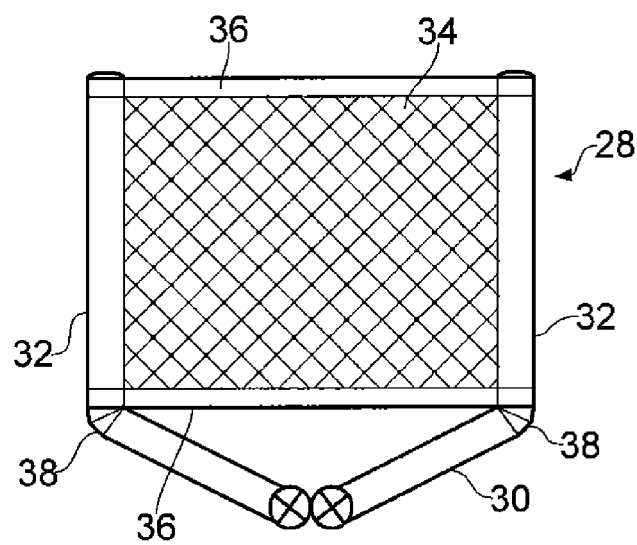
FIG. 5 is a view of the device in the direction of the arrow A in FIG. 4.

FIGS. 4 and 5 show the device 28 in the deployed configuration. As shown in FIG. 5, the device 28 comprises a frame 30 having a pair of parallel members 32 which support a sensor panel 34. The sensor panel 34 comprises a backing member which may comprise a fine gauze or other mesh which supports a paper sheet of sensor material which is impregnated with a universal indicator solution. Spring loaded tension members 36 extend between the members 32 to bias the frame 30 and the sensor panel 34 into a desired configuration.

As shown in FIG. 4, the deployed sensor panel 34 is positioned close to the blade 10. Although not shown, the members 32 of the frame 30 may have locating features which engage the blade 10 to locate the sensor panel 34 precisely with respect to the surface of the blade 10, and at a desired distance from it.

The spacing, or stand-off, of the sensor screen 34 from the surface of the blade 10 is such as to allow the steam, serving as a test fluid, to issue freely from the holes 20 and to impinge on the surface of the sensor panel 34. Each hole 20 that is open will thus produce a jet of steam which, when impinging on the sensor panel 34, will change the state of the indicator solution and so provide a visual indication that the hole 20 in question is open. No steam will issue from a blocked hole 20, and consequently the state of the indicator solution at the respective position on the sensor panel 34 will not change. Any partially blocked or misshaped hole will produce a relatively weak flow of steam, and, in some circumstances, this may show up on the indicator panel as a distorted, mis-positioned, or undersized area on the sensor panel 34 as a result of the change of state of the indicator solution. There is thus at least a qualitative indication of reduced flow through the partially blocked hole.

The sensor panel 34 is exposed to the steam issuing from the holes 20 for a relatively short period, for example approximately 1 second. This is long enough to cause the change of state of the indicator solution at positions directly opposite open holes 20, while avoiding any additional change of state, at regions not directly opposite the holes 20, as a result of diffusion or turbulent interactions in the issuing steam.

The steam supplied to the chamber 16 may, for example, be at a pressure not greater than 0.2 Mpa, for example 0.15 Mpa, above atmosphere, and at a temperature of approximately 120° C. It will be appreciated that, if steam is used as the test fluid, it will be supplied at an elevated temperature, for example up to 200° C., whereas other fluids, such as air with or without any additives to enhance sensing reliability, may be supplied at lower temperatures, for example down to ambient temperature.

The frame 30 may be constructed from interconnected links, including the parallel elements 32, which may be hollow, and provided with an internal cable. Joints 38 between links are formed as cammed structures, so that, depending on the tension t (FIG. 7) applied to the cables, the device 28 transforms between the collapsed and deployed configurations shown in FIGS. 6 and 7. In the collapsed configuration, the device 28 may, for example, be sufficiently slender to fit through a borescope inspection port (typically having a diameter of 2 to 8 mm).

In an alternative embodiment, the sensor screen 34 may comprise other means for responding to impingement of the test fluid. For example, the sensor screen could comprise an electro-mechanical system, such as a MEMS-type (micro-electro-mechanical system) sensor. Such sensors could operate using fibrous deflectors or piezo-electric devices coupled to, or serving as, transducers, which convert deflection, under the influence of the impinging test fluid, to electrical signals.

Regardless of the type of sensor panel 34, the sensor panel response can be analysed to establish the existence, and location, or any blocked, or possibly partially blocked, or misshapen, holes 20. That is to say the sensor panel 34 response can be analysed to assess the condition of holes 20 at the location corresponding to the holes.

It is desirable for the sensor panel 34 to be positioned as close as possible to the surface of the component in which the holes 20 are provided, without causing stagnation of the flow through the holes 20. This is particularly important where the holes 20 in the array are disposed close to one another, in order to enable adequate resolution of the sensor panel response. It is desirable for the sensor panel 34 to be positioned closer to the surface than the separation distance between adjacent holes 20, so that the flow issuing from each hole 20 impinges on the sensor panel 34 before mixing with flow from any other hole. If necessary, the sensor panel 34 can be permeable by the test fluid to avoid stagnation of the flow, or the sensor panel can be inclined so that the jets issuing from the holes 20 impinge obliquely on the sensor panel 34, again to avoid stagnation of the flow. In such circumstances, and also if the jets issuing from the holes 20 are themselves inclined to the surface of the component 8, 10, the shape of the area which responds to the test fluid may be elliptical rather than circular, as is the case when the jets from the holes 20 impinge perpendicularly on the sensor panel 34.

In order to avoid poor sensor response as a result of jets from the holes 20 impinging in an oblique manner on the sensor panel 34, the sensor panel 34 may comprise a plurality of tubes extending normal to the plane of the sensor panel, so that oblique flows are redirected in the normal direction. The tubes may be disposed in an array corresponding to the array of holes in the component 8, 10 so that each hole 20 has a corresponding tube on the sensor panel 34.

In such an embodiment, the vibration of each tube as a result of test fluid impingement, from the respective hole 20 stimulates the respective MEMS sensor.

An advantage of an electro-mechanical sensor system is that the sensor panel 34 would not be a "one-shot" device, but could remain within the engine and displaced from one vane 8 or blade 10 to another as each reading is taken. The response of the sensor panel 34 to each vane 8 or blade 10 could be transmitted to a suitable processor outside the engine for analysis of the data. The response could be in the form of a still or video image calibrated to illustrate absolute or relative exit velocities from each hole. For example, different colours could be used to indicate different flow rates in a still or moving image. By contrast, a sensor panel 34 utilising an absorbent material impregnated with an indicator solution would normally need to be retrieved from the engine after each vane or blade has been tested for either visual analysis of the resulting response, or for analysis by a suitable image capture system. As an alternative, if the image generated by the change of state of the indicator solution is carried through the thickness of the absorbent material so as to be visible from the rear of the sensor panel 34, a "close in" camera system could be used to image the sensor panel response without withdrawing the sensor panel 34 itself. If required, illumination may be supplied, for example via a fibre optic device, to improve the image captured by the camera.

While the present invention has been described with reference to vanes 8 and blades 10, the method and device are equally applicable to the inspection of flow passages of any component, such as, by way of non limiting example, cooling holes of a combustor for a gas turbine engine.

The invention claimed is:

1. A method of inspecting a hole defined by a component situated within an engine, the engine including a chamber configured to receive fluid from a fluid supply, wherein the component is in flow communication with the fluid supply via the chamber, the method comprising:
   (i) delivering a test fluid via the chamber to the component to induce flow of the test fluid through the hole;
   (ii) deploying a sensor panel adjacent to the component in a path of test fluid issuing from the hole, the sensor panel being sensitive to impingement of the test fluid; and
   (iii) assessing a condition of the hole depending on a response of the sensor panel at a location corresponding to the hole.

2. The method of claim 1, wherein the hole is one hole of an array of holes, and the sensor panel is of a size to extend into the path of test fluid issuing from a plurality of the holes of the array.

3. The method of claim 2, wherein the test fluid is steam.

4. The method of claim 1, wherein the sensor panel comprises a sheet impregnated with an indicator composition which changes state upon impingement by the test fluid.

5. The method of claim 4, wherein the sheet comprises a woven or non-woven textile material.

6. The method of claim 4, wherein the sheet comprises paper.

7. The method of claim 1, wherein the sensor panel comprises an array of electro-mechanical transducers, and impingement of the test fluid on a transducer of the array generates an electrical signal.

8. The method of claim 7, wherein the disposition of the transducers in the transducer array corresponds to the disposition of holes in the hole array.

9. The method of claim 1, wherein the sensor panel is supported by a frame.

10. The method of claim 9, wherein the frame is of variable geometry and is transformable between a collapsed condition and a deployed condition.

11. The method of claim 9, wherein the frame has locating means for cooperation with the component to locate the sensor panel with respect to the component.

12. The method of claim 1, wherein the engine is a gas turbine engine.

13. The method of claim 12, wherein the component is an aerofoil component.

14. A device operable to conduct a method in accordance with claim 1, the device comprising the sensor panel sensitive to the impingement of the test fluid.

15. The device of claim 14, in which the sensor panel is supported by a frame of variable geometry.

* * * * *